United States Patent
Peterson

(10) Patent No.: US 6,653,417 B2
(45) Date of Patent: Nov. 25, 2003

(54) CATALYST PRECURSOR AND OLEFIN POLYMERIZATION PROCESSES

(75) Inventor: Thomas H. Peterson, Charleston, WV (US)

(73) Assignee: Univation Technologies, LLC, Houston, TX (US)

( * ) Notice: Subject to any disclaimer, the term of this patent is extended or adjusted under 35 U.S.C. 154(b) by 26 days.

(21) Appl. No.: 09/976,606

(22) Filed: Oct. 12, 2001

(65) Prior Publication Data

US 2003/0105254 A1 Jun. 5, 2003

(51) Int. Cl.$^7$ ............... C08F 4/44; B01J 31/38
(52) U.S. Cl. .......... 526/172; 526/132; 526/161; 502/155; 502/167
(58) Field of Search ............... 502/152, 155, 502/167; 526/161, 171, 132, 172

(56) References Cited

U.S. PATENT DOCUMENTS 6,187,712 B1   2/2001   Peterson ............ 502/152

6,399,725 B1 * 6/2002 Eilerts .................. 526/161

FOREIGN PATENT DOCUMENTS

WO    WO 99/01460    1/1999

OTHER PUBLICATIONS

Cloke et al., "Zirconium Complexes incorporating the New Tridentate Diamide Ligand [(Me$_3$Si)N{CH$_2$Ch$_2$N(SiMe$_3$}$_2$]$^{2-}$(L); the Crystal Structures of [Zr(BH$_4$)$_2$L] and [ZrCl{CH(SiMe$_3$)$_2$}L]" J. Chem Soc. Dalton Trans 1995 25–30 (Jul.).

* cited by examiner

Primary Examiner—Robert Harlan
(74) Attorney, Agent, or Firm—Lisa Kimes Jones; Kevin M. Faulkner

(57) ABSTRACT

Catalyst precursor compounds having both (i) a polydentate ligand which comprises a cyclic moiety as well as a heteroatom and (ii) a protected hydride/hydrocarbyl ligand bonded to a metal atom, as well as olefin polymerization catalyst systems based thereupon, polymerization processes using such catalyst systems and polymers produced thereby.

11 Claims, No Drawings

CATALYST PRECURSOR AND OLEFIN POLYMERIZATION PROCESSES

FIELD OF THE INVENTION

The present invention relates to catalyst precursor compounds having both (i) a polydentate ligand which comprises a cyclic moiety as well as a heteroatom and (ii) a protected hydride/hydrocarbyl ligand linked to a metal atom, to olefin polymerization catalyst systems based thereupon, to polymerization processes using such catalyst systems, and to polymers produced thereby.

BACKGROUND OF THE INVENTION

The intense commercialization of metallocene polyolefin catalysts has led to widespread interest in the design of non-metallocene, homogeneous catalysts. This field is more than an academic curiosity as new, non-metallocene catalysts may provide an easier pathway to currently available products and may also provide product and process opportunities which are beyond the capability of metallocene catalysts. In addition, certain non-cyclopentadienyl ligands may be more economical due to the relative ease of synthesis of a variety of substituted analogs.

Thus there is a need in the art for new olefin polymerization catalysts and the polymers they produce. This invention identifies a new family of catalysts that can be used to produce polyolefins, particularly polyethylenes.

WO 97/02298, WO 96/33202 and Fuhrmann et al, *Inorg. Chem.* 35:6742–6745 (1996), each fully incorporated herein by reference, all disclose nitrogen containing single site like catalyst systems.

WO 99/01460, fully incorporated herein by reference, discloses the use of transition metal compounds comprising bidentate ligands containing pyridine or quinoline moieties and mixtures thereof with activators to polymerize olefins. For example, [[1-(2-pyridyl)N-1-methylethyl]-[1-N-2,6-diisopropylphenylamido]]zirconium tribenzyl is combined with modified methyl alumoxane in the gas phase to produce ethylene/hexene copolymers.

Furthermore, U.S. Pat. No. 6,187,712 B1, fully incorporated herein by reference, discloses a catalyst composition for the polymerization of olefins that comprises a mono- or biscyclopentadienyl catalyst precursor comprising at least one protected hydride and/or protected hydrocarbyl ligand such as tetrahydroborate bound to a metal atom. A typical example of a catalyst precursor disclosed in the patent is methylcyclopentadienylzirconium tris(tetrahydroborate).

It has now been found that transition metal compounds comprising both polydentate, heteroatom containing ligands and protected hydride and/or hydrocarbyl ligands combined with a cocatalyst can effectively catalyze the polymerization of olefins.

SUMMARY OF THE INVENTION

The present invention provides catalyst precursor compound represented by $MX_xY_yZ_z$ wherein M is a metal selected from Groups 3 to 12 and the lanthanide and actinide series of the Periodic Table of Elements. X represents an anionic moiety of the formula $AR_4$, where A represents a Group 13 element, the radicals R are independently selected from carbon containing groups and hydrogen. Also, two radicals R may be combined to form a ring structure together with A. Moreover, at least one of the radicals R bridges A and M. Y is an at least bidentate anionic group represented by $(T)_t$—D—$(E)_e$—G wherein D is selected from elements of Groups 13 to 16 and is bonded to M. G is a 3- to 30-membered mono- or polycyclic radical and comprises, and is bonded to M through, a heteroatom Q which either is a ring member or is covalently bonded to a ring member. Furthermore, E bridges D and G and may additionally be bonded to M, whereas T is a radical comprising 1 to 50 non-hydrogen atoms. e is 0 or 1 and t is 0 or an integer sufficient to satisfy the valence of D. Z is a monovalent, divalent or trivalent anion different from X and Y. x is an integer of from 1 to 6 inclusive, y is an integer of from 1 to 3 inclusive and z is 0 or a positive integer, provided that x times the valence of X plus y times the valence of Y plus z times the valence of Z equals the valence of M.

The present invention also provides a catalyst system which includes the catalyst compound, for polymerization processes utilizing the catalyst system, and for polymers produced therefrom.

DETAILED DESCRIPTION OF THE INVENTION

For the purposes of this patent specification, the term "catalyst" refers to a metal compound, that when combined with an activator, polymerizes olefins. The term "activator" is used interchangeably with the term "co-catalyst", and the term "catalyst system" refers to the combination of a catalyst, an activator, and optionally a support material.

In one embodiment, the new catalyst compounds of the present invention may be represented by Formula I:

$$MX_xY_yZ_z \qquad \text{Formula I}$$

In Formula I, M is a metal selected from Groups 3 to 12 and the lanthanide and actinide series of the Periodic Table of Elements. In one embodiment, M is selected from Groups 3 to 10 and the lanthanides. Illustrative, non-limiting examples of M are Ti, Zr, Hf, V, Nb, Ta, Cr, Mo, W, Ni, Co, Fe, Pd, Ce, Y and Sm. Preferably, M is selected from Groups 4, 5, 6 and the lanthanides, in particular from Groups 4 and 5. Preferably, M is a Group 4 element, preferably zirconium or hafnium, and most preferably M is zirconium.

In Formula I, X represents a anionic moiety having the formula $AR_4$ where at least one of the radical groups, R, bridge A and M and where A is selected from Group 13 elements such as, e.g., B, Al and Ga. Preferably, A represents B or Al, and most preferably B. The radicals R, may be the same or different from each other, and are independently be hydrogen or a $C_{1-20}$ hydrocarbyl radical. Preferably, each R is independently hydrogen, an alkyl group, for example methyl or ethyl, or an aryl group, for example phenyl. More preferably at least one, and even more preferably at least two of the radicals R are hydrogen. Most preferably three or four of the radicals R are hydrogen.

Moreover, in compounds of Formula I the two radicals R and A together may form a ring having 3 to 10 ring members, preferably 4 to 8 members. While for values of x of 2 and higher the radicals X in Formula I may be identical or different, they are preferably identical.

In a preferred embodiment, $AR_4$, represented by each X in Formula I, is independently tetrahydroborate or tetrahydroaluminate. Most preferably each radical X is tetrahydroborate.

In Formula I, Y is an at least bidentate anionic group represented by Formula II:

$$(T)_t\text{-D}—(E)e\text{-G} \qquad \text{Formula II}$$

Where D is bonded to M of Formula I, and is selected from elements of Groups 13 to 16 of the Periodic Table of Elements. Illustrative, non-limiting examples of atoms D are B, C, Si, N, P, O and S. Preferably D is selected from N and P. Most preferably, D is nitrogen.

In Formula II, G is a mono- or polycyclic (e.g., bicyclic or tricyclic) radical, containing a heteroatom Q. G is bonded to M through the heteroatom Q which is either a ring member or is covalently bonded to a ring member. G contains at least 3, preferably at least 5, and most preferred at least 6 ring members. The maximum number of ring members of G is about 30, more preferred about 20, and most preferred about 10. Preferably G is not more than bicyclic, and most preferred it is monocyclic. If the ring system is polycyclic, it preferably comprises fused rings. In another embodiment, G is an aromatic ring system or fused ring system or at least comprises an aromatic ring. G may contain additional heteroatoms as ring members and/or covalently bonded to the ring other than Q. Preferably Q is a ring member and is N, O, P or S, more preferably N or P and most preferably N. In one embodiment, at least one of D and Q is N. In a particularly preferred embodiment D and Q are both nitrogen atoms. If Q is bonded to a ring member, this ring member usually is a carbon atom. Illustrative, non-limiting examples of $G_Q$ are pyridyl, pyrazyl and quinolyl, with pyridyl being particularly preferred.

In addition to optionally comprising more than one heteroatom as a ring member or covalently bonded to a ring member, G may also carry one or more (e.g., 2, 3, 4 etc.) substituents in any position of the ring(s) thereof. Illustrative, non-limiting examples of preferred substituents are linear, branched and cyclic alkyl and alkenyl, alkoxy, aryl, alkylaryl, arylalkyl and aryloxy radicals.

E, if present (i.e., e in Formula II equals 1), bridges D and G. If Q is a ring member, E preferably connects D and an atom different from Q, for example, a ring atom adjacent to Q. The number of atoms belonging to E and separating D from G usually is such that the ring structure formed by M, one or more atoms of G, E and D has at least 4, preferably at least 5 members, and not more than 8, preferably not more than 7, and most preferred not more than 6 ring members. Usually at least one of the atoms of E which connects D and G is selected from elements of Group 14, in particular C and Si. In addition to being bonded to G and D, E may also be bonded to M. Moreover, one or more atoms of E and one or more atoms of G together may form an additional ring structure, for example a ring fused with G. Additionally or alternatively, one or more atoms of E may form a ring together with D and, optionally, with one or more atoms of T. If present, the rings formed by E or parts thereof and G or parts thereof and the rings formed by E or parts thereof and D and, optionally, T and parts thereof usually have not more than 8 ring members, preferably not more than 7 ring members, most preferred not more than 6 ring members. Furthermore, these rings may be unsaturated or even (hetero)aromatic.

Non-limiting examples of E include groups of the formulae $(CR^1R^2)$, $(C=CR^1R^2)$ and $(SiR^1R^2)$ wherein $R^1$ and $R^2$ are independently selected from hydrogen and $C_1-C_{20}$ hydrocarbyl groups, in particular $C_1-C_{10}$ hydrocarbyl groups such as, e.g., alkyl and aryl groups. $R^1$ and $R^2$ may be the same or different from each other. Preferred radicals $R^1$ and $R^2$ are hydrogen, methyl, ethyl, propyl and phenyl, with methyl being particularly preferred. Further illustrative, non-limiting examples of E include groups of the formulae $—CR^1=CR^2—$ and $—CR^1R^2—SiR^1R^2—$ wherein $R^1$ and $R^2$ have the meanings given above.

In Formula II, T is a radical comprising 1 to 50 non-hydrogen atoms. Preferably T comprises at least 2, more preferred at least 4, and most preferred at least 6, non-hydrogen atoms whereas the maximum number of non-hydrogen atoms included in T usually does not exceed 40, preferably not exceed 30 and most preferred not exceed 20. Usually at least one of these non-hydrogen atoms is carbon and preferably at least 50%, most preferred at least 75% and up to 100%, of these non-hydrogen atoms are carbon atoms. Of course, hydrogen atoms may also be (and preferably are) present in T. Preferred examples of T include unsubstituted and substituted $C_1-C_{20}$ hydrocarbyl groups (such as, e.g. $C_6-C_{20}$ hydrocarbyl groups) and tri($C_1-C_{20}$ hydrocarbyl) silyl groups (e.g., tri($C_1-C_6$ alkyl)silyl groups) and combinations thereof. Even more preferred examples of T include groups which comprise at least one cyclic or heterocyclic radical, for example, substituted aryl and heteroaryl groups. Usually these groups comprise 5 to 20 (e.g., 6 to 10) ring members. Preferred aryl and heteroaryl groups carry at least one and, even more preferred, two substituents in ortho position with respect to D (in addition to one or more optional meta- and/or para-substituents). These one or two ortho-substituents may, for example, be halogen atoms (e.g., Cl, Br), $C_1-C_{20}$ hydrocarbyl groups (e.g., $C_3-C_{20}$ alkyl and $C_6-C_1$ aryl, alkylaryl or arylalkyl groups such as isopropyl, isobutyl, sec-butyl, tert-butyl, phenyl, benzyl, tolyl, xylyl and naphthyl) and tri($C_1-C_{20}$ hydrocarbyl)silyl groups (preferably trialkylsilyl groups such as trimethylsilyl radicals). If two ortho-substituents are present, they are preferably identical. Furthermore, if T comprises a heteroaryl moiety, this moiety preferably comprises one or more heteroatoms independently selected from O, N and S. Particularly preferred examples of T are phenyl groups carrying two ortho-substituents selected from isopropyl, isobutyl, sec-butyl, tert-butyl, phenyl, benzyl, tolyl, naphthyl and trimethylsilyl radicals. The most preferred ortho-substituent is isopropyl.

If two or more groups T are present, they are preferably identical. However for t=0, T is absent (e.g., for D=oxygen). In preferred embodiments of the compound of Formula I not more than two and, most preferred, only one group T is present in the group of Formula II (e.g., for D=N).

In Formula II, Z represents a monovalent, divalent or trivalent anion that is bonded to M and is different from X and Y. If two or more anions Z are present, they may be identical or different. Illustrative, non-limiting examples of Z are halogen, alkyl, aryl, alkenyl, alkylaryl and arylalkyl radicals having 1–20 carbon atoms (optionally bonded to M through an oxygen atom). Further non-limiting examples of Z are amide, phosphide, sulfide, silylalkyl, diketonate, and carboxylate groups. Preferably Z is selected from halogen, alkyl and arylalkyl radicals. Moreover, it is to be noted that the presence of Z in the compounds of the present invention is optional.

The values of x, y and z in Formula I are such that a neutral compound results. Furthermore, in particularly preferred compounds of Formula I, y=1 and z=0, particularly if Y is a bidentate ligand and M is a Group 4 element.

In a particularly preferred embodiment the catalyst precursor compound of the invention is represented by the formula $MX_xY_y$ where M is titanium, zirconium or hafnium and X represents an anionic moiety of the formula $BR_4$, where two of the radicals R represent hydrogen and the remaining radicals R are independently $C_1-C_{10}$ hydrocarbyl groups or hydrogen atoms and at least one of the radicals R bridges B and M. Also, two radicals R may be combined to form a ring structure together with B. In this preferred embodiment, Y is an at least bidentate anionic group of the formula T—N—E—G wherein N is bonded to M, G is a 5- to 20-membered mono- or bicyclic radical comprising a ring member Q which is selected from N, O, S and P and connects G to M, and E represents $(CR^1R^2)$, $(C=CR^1R^2)$ and $(SiR^1R^2)$, with $R^1$ and $R^2$ being aliphatic and/or aromatic $C_1$–$C_{10}$ groups. T is an aryl or heteroaryl group having at least one substituent in ortho position with respect to D, the at least one substituent being selected from $C_3$–$C_{20}$ alkyl, $C_6$–$C_{10}$ aryl and trialkylsilyl groups. Furthermore, x is an integer of from 1 to 4 inclusive and y is 1 or 2, provided that x times the valence of X plus y times the valence of Y equals the valence of M. In an even more preferred embodiment, M is zirconium, X represents $BH_4$, G is pyridyl, E is $C(CH_3)_2$, T is 2,6-diisopropylphenyl, x is 3 and y is 1.

Unless otherwise stated, a reference to a compound or component includes the compound or component by itself, any of its individual stereoisomers and any mixtures thereof, as well as any combination with other compounds or components, such as mixtures of compounds.

As utilized herein, the following terms have the meanings indicated below.

The term "alkyl", means a straight-chain, branched-chain or cyclic alkyl radical. Examples of such radicals include, but are not limited to, methyl, ethyl, n-propyl, isopropyl, n-butyl, isobutyl, sec-butyl, tert-butyl, pentyl, iso-amyl, hexyl, 2-ethylhexyl, octyl, cyclopentyl, cyclohexyl and the like. The cyclic alkyl radicals may be substituted with one or more straight-chain and/or branched-chain alkyl radicals (i.e., may be alkylcycloalkyl radicals such as, e.g., methylcyclohexyl etc.). Conversely, the straight-chain and branched-chain alkyl radicals may be substituted with one or more cyclic alkyl radicals (i.e., may be cycloalkylalkyl radicals such as cyclohexylmethyl etc.). Moreover, unless indicated otherwise, the above alkyl radicals may be substituted by one or more groups preferably and independently selected from halogen (e.g., F, Cl, Br), alkoxy (e.g., methoxy, ethoxy, propoxy, butoxy and the like), hydroxy, amino, monoalkylamino (e.g., methylamino, ethylamino, propylamino and the like) and dialkylamino (e.g., dimethylamino, diethylamino, dipropylamino, diisopropylamino, piperidino and the like) and trihydrocarbylsilyl (e.g., trimethylsilyl, triphenylsilyl and the like). Unless otherwise stated, the above definition of the term "alkyl" also applies to groups which comprise one or more alkyl radicals.

Preferred alkyl groups are linear and branched groups having 1 to 8, particularly 1 to 6, and even more preferred, 1 to 4 carbon atoms (such as, e.g., methyl, ethyl, propyl and isopropyl). If present, substituents are preferably selected from halogen and alkoxy, more preferred from F, Cl, methoxy and ethoxy, most preferred from F and Cl.

The term "alkenyl" means "alkyl" as defined above having one or more double and/or triple bonds. Examples of alkenyl radicals include, but are not limited to, ethenyl, propenyl, allyl, butenyl, propargyl, 1,4-butadienyl, isopropenyl, cyclopentenyl, cyclohexenyl, cyclooctenyl, cyclopentadienyl, cyclohexadienyl, cyclooctadienyl and the like. Preferred alkenyl groups are those having 2 to 8, particularly 2 to 6, and even more preferred, 2 to 4 carbon atoms (such as, e.g., vinyl, allyl, and 2-butenyl). If present, substituents are preferably selected from halogen and alkoxy, more preferred from F, Cl, methoxy and ethoxy, most preferred from F and Cl.

The term "alkoxy" means an alkyl or alkenyl ether radical wherein the terms "alkyl" and "alkenyl" are as defined above. Examples of suitable alkyl ether radicals include, but are not limited to, methoxy, ethoxy, n-propoxy, isopropoxy, n-butoxy, iso-butoxy, sec-butoxy, tert-butoxy, allyloxy, trifluoromethoxy and the like. Preferred alkoxy groups are methoxy and ethoxy.

The term "aryl" means an aromatic radical, for example, a phenyl, naphthyl, phenanthryl or anthracenyl radical and the like which optionally carries one or more identical or different substituents, for example, alkoxy, aryl, halogen, hydroxy, amino, monoalkylamino, dialkylamino, nitro, trihydrocarbylsilyl, alkyl-CO, alkylsulfonyl, alkyl-OCO etc., these terms being as defined herein. Illustrative, non-limiting examples of aryl radicals are phenyl, naphthyl, fluorenyl, chlorophenyl, dichlorophenyl, fluorophenyl, perfluorophenyl, hydroxyphenyl, anisyl, biphenyl, nitrophenyl, acetylphenyl, aminophenyl, and the like. Unless otherwise stated, the above definition of the term "aryl" also applies to groups which comprise one or more aryl radicals. For example, the term "aryloxy" means an aryl ether radical wherein the term "aryl" is as defined above. Preferred aryl groups contain 6 to 12, more preferred 6 to 10 carbon atoms, such as, e.g., phenyl, naphthyl and biphenyl. Preferred aryloxy groups are phenoxy and naphthoxy.

The term "alkylaryl" means an aryl radical carrying at least one alkyl and/or alkenyl radical as ring substituent, the terms "aryl", "alkyl" and "alkenyl" being as defined above. Illustrative, non-limiting examples of alkylaryl groups are tolyl, xylyl, mesityl, ethylphenyl, trifluoromethylphenyl, vinylphenyl, cumyl and the like.

The term "arylalkyl" means an alkyl radical carrying at least one aryl group wherein the terms "aryl" and "alkyl" are as defined above, provided that the aryl radical may have one or more alkyl substituents. Illustrative, non-limiting examples of arylalkyl groups are benzyl, phenethyl, diphenylmethyl, tolylmethyl, naphthylmethyl and the like. Preferred examples of arylalkyl and alkylaryl groups include benzyl, phenethyl, tolyl and xylyl.

The term "halogen" means fluorine, chlorine, bromine and iodine. Preferred halogens are fluorine, chlorine and bromine.

The term "hydrocarbyl" encompasses alkyl, alkenyl, arylalkyl and alkylaryl groups as defined above. Preferred hydrocarbyl groups comprise 1 to 20, more preferred 1 to 10, and most preferred 1 to 6 carbon atoms. Illustrative, non-limiting examples are methyl, ethyl, propyl, benzyl and phenyl.

The catalyst systems of the present invention comprise one or more catalyst precursor compounds described above and at least one activator or co-catalyst. The activator may be any known catalyst activator and may include an alkyl aluminum compound, an alumoxane, a modified alumoxane, a non-coordinating anion, a Lewis acid, a borane or a mixture thereof.

There are a variety of methods for preparing alumoxanes and modified alumoxanes, illustrative, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253 and 5,731,451 and European publications EP-A-0 561 476, EP-B1-0 279 586 and EP-A-0 594-218, and PCT publication WO 94/10180, all of which are filly incorporated herein by reference. Methylalumoxane (MAO), modified methylalumoxane (MMAO), and trisobutylalumoxane are among the preferred cocatalysts.

Ionizing compounds which give rise to noncoordinating anions may contain an active proton, or some other cation associated with, but not coordinated to or only loosely coordinated to the remaining ion of the ionizing compound.

Such compounds and the like are described in European publications EP-A-0 570 982, EP-A-0 520 732, EP-A-0 495 375, EP-A-0 426 637, EP-A-500 944, EP-A-0 277 003 and EP-A-0 277 004, and U.S. Pat. Nos. 5,153,157, 5,198,401, 5,066,741, 5,206,197, 5,241,025, 5,387,568, 5,384,299 and 5,502,124 and U.S. patent application Ser. No. 08/285,380, filed Aug. 3, 1994, all of which are filly incorporated herein by reference. Non-limiting examples of further cocatalysts include those described in PCT publication WO 98/07515 (fully incorporated herein by reference) such as tris(2,2',2"-nonafluorobiphenyl)fluoroaluminate. Combinations of activators are also contemplated by the invention, for example, alumoxanes and ionizing activators in combination, see for example, PCT publications WO 94/07928 and WO 95/14044 and U.S. Pat. Nos. 5,153,157 and 5,453,410 all of which are fully incorporated herein by reference. Methods of activation such as using radiation and the like are also contemplated as cocatalysts for the purposes of this invention.

Illustrative, non-limiting examples of preferred cocatalysts are the following: tris(2,2',2"-nonafluorobiphenyl) fluoroaluminate, alumoxane (e.g., MAO and MMAO), triphenyl boron, triethyl boron, tri-n-butyl ammonium tetraethylborate, triaryl borane, tetrakis(pentafluorophenyl) borate salts (such as, e.g., tri(n-butyl)ammonium tetrakis (pentafluorophenyl)borate), trisperfluorophenyl boron, diethylaluminum chloride and diisobutylaluminum chloride.

When the cocatalyst is an aluminum compound such as, e.g., an alumoxane, the ratio of Al to M in the catalyst precursor compound usually is at least about 2:1, preferably at least about 10:1, most preferred at least about 50:1. On the other hand, the ratio Al:M usually is not higher than about 100,000:1, preferably not higher than about 10,000:1, and most preferred not higher than about 2,000:1.

On the other hand, when the cocatalyst is a noncoordinating anion (NCA), the ratio of NCA to M usually is at least about 0.5:1, preferably at least about 1:1, although this ratio usually is not higher than about 10:1, preferably not higher than about 5:1.

The catalyst precursor compound of Formula I may be synthesized by any method known in the art. For example, WO 99/01460, supra, discloses methods to produce these compounds. An exemplary process for making preferred compounds of the present invention comprises the reaction of a tetrahydroborate complex of formula $M(BH_4)_n$, where n is the oxidation state of M (prepared, for example, by reaction of the corresponding halide of M with an alkali or alkaline earth tetrahydroborate), with an alkali or alkaline earth metal salt of Y in the desired stoichiometric ratio. Such a process is illustrated in Example 2 below for M=Zr.

In a particularly preferred embodiment of the present invention, the catalyst precursor compound is N-(1-methyl-1-(2-pyridyl)ethyl)-N-(2,6-diisopropylphenyl) amido zirconium tris(tetrahydroborate). In another preferred embodiment, N-(1-methyl-1-(2-pyridyl)ethyl)-N-(2,6-diisopropylphenyl)amido zirconium tris(tetra-hydroborate) is used in combination with an alumoxane, preferably methylalumoxane, more preferably modified methylalumoxane, in a gas or slurry phase reactor to produce polyethylene, preferably high density polyethylene. In another preferred embodiment, a non-coordinating anion, such as tri(n-butyl)ammonium tetrakis(pentafluorophenyl) boron or a compound such as tris(perfluorophenyl)-boron, is used in combination with the N-(1-methyl-1-(2-pyridyl) ethyl)-N-(2,6-diisopropylphenyl)amido zirconium tris (tetrahydroborate) in a gas or slurry phase reactor. In another embodiment that activator is selected from the following: tris(2,2',2"-nonafluorobiphenyl)fluoroaluminate, methyl alumoxane, triphenyl boron, triethylboron, tri-n-butylammonium tetraethylborate, triaryl-borate, tri(n-butyl) ammonium tetrakis(pentafluorophenyl)boron, tris (perfluoro-phenyl)boron and diethylaluminum chloride.

One or more of the catalyst components may be supported on an organic or inorganic support. Typically the support can be of any of the known solid, porous supports. Non-limiting examples of typical support materials include talc; inorganic oxides such as silica, magnesium chloride, alumina, silica-alumina and the like; and polymeric supports such as polyethylene, polypropylene, polystyrene and the like. Preferred supports include silica, clay, talc, magnesium chloride and the like. Preferably the support is used in finely divided form. Prior to use the support is preferably partially or completely dehydrated. The dehydration may be done physically by calcining or by chemically converting all or part of the active hydroxyls. For more information on how to support catalysts and catalyst components, respectively, U.S. Pat. No. 4,808,561 (fully incorporated herein by reference) may, for example, be referred to.

If both the catalyst precursor and the cocatalyst are to be supported, the cocatalyst may be placed on the same support as the catalyst precursor or may be placed on a separate support. Also, the components of the catalyst system need not be fed into the reactor in the same manner. For example, one catalyst component may be slurried into the reactor on a support while the other catalyst component may be provided in a solution.

In another embodiment the catalyst system is fed into the reactor in a solution or slurry. Hydrocarbons are useful for the solutions or slurries. For example, the solution or slurry carrier may comprise toluene, hexane, isopentane or a combination thereof such as toluene and isopentane or toluene and pentane. A typical solution would be 0.02 to 0.05 mole catalyst in the hydrocarbon carrier, preferably isopentane or hexane.

In another embodiment the carrier for the catalyst system or its components is a supercritical fluid, such as ethane or propane. For more information on supercritical fluids as catalyst feed agents see EP 0 764 665 A2, fully incorporated herein by reference.

Polymerization Process of the Invention

The catalyst systems described above are suitable for use in a solution, gas or slurry polymerization process or a combination thereof, most preferably a gas or slurry phase polymerization process.

In one aspect, this invention is directed toward solution, slurry or gas phase polymerization reactions involving the polymerization of one or more ethylenically unsaturated monomers (olefins) preferably having 2 to 30 carbon atoms, more preferably 2 to 12 carbon atoms, and most preferably 2 to 8 carbon atoms. Preferred monomers include one or more of ethylene, propylene, butene-1, pentene-1, 4-methyl-pentene-1, hexene-1, octene-1, decene-1 and 3-methyl-pentene-1. Cyclic and aromatic olefins such as cyclohexene, norbornene and styrene may also be used. Other non-limiting examples of suitable monomers include diolefins, for example, conjugated and non-conjugated dienes and polyenes such as norbornadiene, vinyl norbornene and ethylidene norbornene. In one aspect, a homopolymer of ethylene is produced. In another aspect, a copolymer of ethylene and one or more of the monomers listed above is produced.

In another aspect, ethylene and/or propylene are polymerized with at least two different comonomers to form a terpolymer. The preferred comonomers are a combination of alpha-olefin monomers having 4 to 10 carbon atoms, more preferably 4 to 8 carbon atoms, optionally with at least one diene monomer. The preferred terpolymers include combinations such as ethylene/butene-1/hexene-1, ethylene/propylene/butene-1, propylene/ethylene/hexene-1, ethylene/propylene/norbornene and the like.

In yet another aspect, the process of the invention involves the polymerization of ethylene and at least one comonomer having 4 to 8 carbon atoms, preferably 4 to 7 carbon atoms. Particularly, the comonomers are butene-1, 4-methyl-pentene-1, 3-methyl-pentene-1, hexene-1 and octene-1, the most preferred being hexene-1, butene-1 and octene-1.

Typically in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228, all of which are fully incorporated herein by reference.)

The reactor pressure in a gas phase process usually is at least about 10 psig (69 kPa), preferably at least about 100 psig (690 kPa), more preferred at least about 200 psig (1379 kPa) and most preferred at least about 250 psig (1724 kPa). On the other hand, the reactor pressure usually is not higher than to about 500 psig (3448 kPa), preferably not higher than about 400 psig (2759 kPa), more preferably not higher than about 350 psig (2414 kPa).

The reactor temperature in the gas phase process usually is at least about 30° C., preferably at least about 60° C., more preferably at least about 70° C., while it usually is not higher than about 120° C., preferably not higher than about 115° C., more preferably not higher than about 110° C., and most preferably not higher than about 95° C. When high density polyethylene is desired the reactor temperature is typically from about 70 to about 105° C.

The productivity of the catalyst or catalyst system in a gas phase system is influenced by the main monomer partial pressure. The preferred mole percentage of the main monomer (for example, ethylene or propylene), preferably ethylene, is from about 25 to about 90 mole percent. Generally, the comonomer partial pressure is in the range of from about 20 psia (138 kPa) to about 300 psia (517 kPa), preferably about 75 psia (517 kPa) to about 300 psia (2069 kPa), which are typical conditions in a gas phase polymerization process. Also in some systems the presence of comonomer can provide an increase in productivity.

Other gas phase processes contemplated by the present invention, by way of non-limiting example, include those described in U.S. Pat. Nos. 5,627,242, 5,665,818 and 5,677,375, and European publications EP-A-0 794 200, EP-A-0 802 202 and EP-B-634 421, all of which are herein fully incorporated by reference.

A slurry polymerization process generally uses pressures in the range of from about 1 to about 50 atmospheres (103 kPa to 5068 kPa) and even greater and temperatures in the range from about 0° C. to about 120° C. In a slurry polymerization, a suspension of solid, particulate polymer is formed in a liquid polymerization diluent medium to which ethylene and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

Another aspect of the process of the invention is where the process, preferably a slurry or gas phase process, is operated in the absence of or essentially free of any scavengers, such as triethylaluminum, trimethylaluminum, tri-isobutylaluminum and tri-n-hexylaluminum and diethyl aluminum chloride, dibutyl zinc and the like. This process is described in PCT publication WO 96/08520 and U.S. Pat. No. 5,712,352, which are herein fully incorporated by reference.

In another aspect, the process is run with scavengers. Typical scavengers include trimethyl aluminum, tri-isobutyl aluminum and an excess of alumoxane or modified alumoxane.

The molecular weight distribution (Mw/Mn), flow index, and/or density of the polymer made may, for example, be controlled by altering the reaction temperature and/or the catalyst concentration in the intimately mixed catalyst solution and/or the hydrogen concentration and/or the cocatalyst to transition metal ratio, such as the aluminum/zirconium ratio.

In one aspect, the polyolefin recovered typically has a melt index as measured by ASTM D-1238, Condition E, at 190° C. of about 1 g/10 min or less. In another aspect, the polyolefin is ethylene homopolymer or copolymer. The comonomer is preferably a $C_3$ to $C_{20}$ linear, branched or cyclic monomer, and in one embodiment is a $C_3$ to $C_{12}$ linear or branched alpha-olefin, preferably propylene, hexene, pentene, hexene, heptene, octene, nonene, decene, dodecene, 4-methyl-pentene-1, 3-methyl pentene-1, 3,5,5-trimethyl hexene-1, and the like.

In another aspect, the catalyst system described above is used to make a high density polyethylene having a density of from about 0.925 to about 0.965 $g/cm^3$ (as measured by ASTM 2839), and/or a melt index of about 1.0 or less g/10 min or less (as measured by ASTM D-1238, Condition E, at 190° C.). In another aspect, the catalyst system described above is used to make a polyethylene having a density of from about 0.85 to about 0.924 $g/cm^3$.

In yet another aspect, the polymer produced by the process of this invention has a molecular weight distribution (Mw/Mn) of at least 8, e.g., at least 10, more preferably at least 15, even more preferably at least 20, most preferably at least 30. Mn and Mw are measured by gel permeation chromatography.

The polyolefins of the invention can be made into articles such as, by way of non-limiting example, films, molded articles, sheets, pipes and the like. The films may be formed by any of the conventional technique known in the art including extrusion, co-extrusion, lamination, blowing and casting. The films may be obtained by the flat film or tubular process which may be followed by orientation in an uniaxial direction or in two mutually perpendicular directions in the plane of the film. Particularly preferred methods to form the polymers into films include extrusion or coextrusion on a blown or cast film line.

The polymers produced may further contain additives such as slip, antiblock, antioxidants, pigments, fillers, antifog, UV stabilizers, antistats, polymer processing aids, neutralizers, lubricants, surfactants, pigments, dyes and nucleating agents. Non-limiting examples thereof include silicon dioxide, synthetic silica, titanium dioxide, polydimethylsiloxane, calcium carbonate, metal stearates, calcium stearate, zinc stearate, talc, $BaSO_4$, diatomaceous earth, wax, carbon black, flame retarding additives, low molecular weight resins, glass beads and the like. The additives may be present in the typically effective amounts well known in the art, such as 0.001 weight % to 10 weight %.

For purposes of this specification, when an amount, concentration, or other value or parameter, is given as a list of upper preferable values and lower preferable values, this is to be understood as specifically disclosing all ranges formed from any pair of an upper preferred value and a lower preferred value, regardless whether ranges are separately disclosed. Moreover, the upper and lower values of any two ranges given for a specific parameter are to be understood as also disclosing the ranges formed by combining the lower value of the first range with the upper value of the second range and vice versa.

In the present specification, unless otherwise stated, all percentages, parts, ratios, etc., are by weight.

In order to provide a better understanding of the present invention including representative advantages thereof, the following examples are offered.

EXAMPLES

Example 1

Preparation of N-(1-methyl-1-(2-pyridyl)ethyl)-N-(2,6-diisopropylphenyl)amine

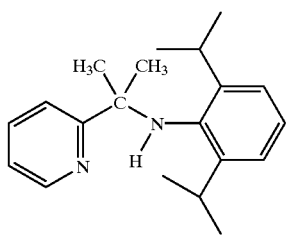

In a dry box, 22.45 mmol (6.34 g) of 2-acetylpyridine(2,6-diisopropylphenylimine) were charged to a 250 mL round bottom flask equipped with a stir bar and septa. The flask was sealed, removed from the dry box and placed under nitrogen purge. Dry toluene (50 mL) was added and stirred to dissolve the ligand. The vessel was chilled to 0° C. in a wet ice bath. Trimethyl aluminum (Aldrich, 2.0 M in toluene) was added dropwise over ten minutes. The temperature of the reaction was not allowed to exceed 10° C. When addition of the trimethyl aluminum was complete, the mixture was allowed to warm slowly to room temperature, and then was placed in an oil bath and heated to 40° C. for 25 minutes. The vessel was removed from the oil bath and placed in an ice bath. A dropping funnel containing 100 mL of 5% KOH was attached to the flask. The caustic was charged to the reaction dropwise over a 1 hour span. The mixture was transferred to a separatory funnel. The aqueous layer was removed. The solvent layer was washed with 100 mL water, then 100 mL brine. The red-brown liquid product was dried over $Na_2SO_4$, vacuum stripped and placed under high vacuum overnight. 80 mL of red-brown liquid was transferred to a 200 mL Schlenk flask equipped with a stir bar. A distillation head with a dry ice condenser was attached to the flask. The mixture was vacuum distilled yielding approximately 70 g of dark yellow viscous liquid product.

Example 2

Preparation of N-(1-methyl-1-(2-pyridyl)ethyl)-N-(2,6-diisopropylphenyl)amido zirconium tris (tetrahydroborate)

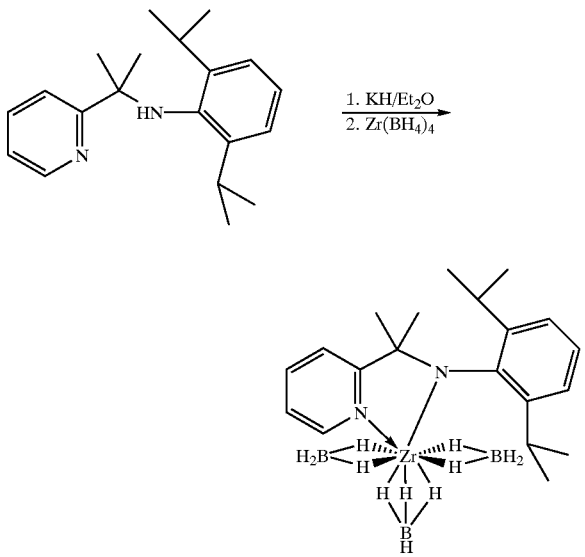

In an oven-dried 250 mL Schlenk flask under an atmosphere of dry argon was placed a slurry of potassium hydride (417 mg, 10.4 mmol) in 100 mL diethyl ether. The slurry was cooled to 0° C. and a solution of [1-(2-pyridyl)N-1-methylethyl][1-N-2,6-diisopropylphenyl]amine (3.08 g, 10.4 mmol) in 20 mL ether was added via syringe. Upon completion of the addition, the stirred slurry was warmed to room temperature. In a separate 250 mL Schlenk flask were placed zirconium tetrachloride (2.42 g, 10.4 mmol) and $LiBH_4$ (906 mg, 41.6 mmol). The dry solid mixture was cooled to −78° C. under Ar and 50 mL of ether was added via syringe. The zirconium reaction slurry was stirred for one hour while warming to room temperature. Both reaction flasks were then connected, cooled in liquid $N_2$ and evacuated on a Schlenk manifold. The liquid nitrogen bath was removed from the flask containing $Zr(BH_4)_4$ and the volatile components were condensed via vacuum transfer in the flask containing the deprotonated N-(1-methyl-1-(2-pyridyl) ethyl)-N-(2,6-diisopropylphenyl)amine. After stirring overnight at room temperature, the volatile materials were removed in vacuo and the crude product was extracted into toluene/pentane. After filtration through a Celite pad, the solvent was removed under vacuum and the residue was recrystallized from toluene/pentane at −35° C. to afford 1.02 g (2.37 mmol) of the title compound in 23% yield from a single crop. Several additional crops were obtained but the yields were not recorded. $^1H$ NMR ($C_6D_6$): δ 8.57 (m, 1H,), 7.07 (m, 3H), 6.78 (m, 1H), 6.42 (m, 1H), 6.36 (m, 1H), 3.50 (septet, J=6.0 Hz, 2H), 2.16 (br 1:1:1:1 quartet, 12H), 1.43 (d, J=6.3 Hz, 6H), 1.08 (s, J=6.3 Hz, 6H), 1.00 (s, 6H) ppm.

The crystal structure of the title compound demonstrates an $\eta^2,\eta^2,\eta^3$-coordination of the borohydride ligands. The molecule shows overall trigonal bipyramidal symmetry with two $\eta^2$-borohydrides positioned symmetrically about the equatorial plane and the $\eta^3$-borohydride ligand lying trans to the axial pyridine. Important bond lengths (Å) and angles (degrees) are given below.

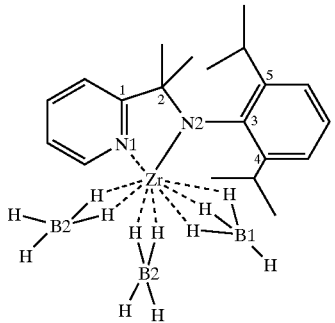

| | |
|---|---|
| Zr-N1 | 2.293 |
| N1-C1 | 1.327 |
| C1-C2 | 1.519 |
| C2-N2 | 1.500 |
| Zr-N2 | 2.047 |
| N2-C3 | 1.475 |
| Zr-C3 | 3.063 |
| Zr-C4 | 3.836 |
| Zr-C5 | 3.836 |
| N1-Zr-N2 | 73.2 |
| Zr-B1 $\eta^3$ | 2.306 |
| B1-$H^{ag}$ | 1.134 |
| B1-H | 1.083 |
| Zr-$H^{ag}$ | 1.971 |
| Zr-B2 | 2.481 |
| B2-$H^{ag}$ | 1.169 |
| B2-H | 0.958 |
| Zr-$H^{ag}$ | 2.033 |
| N1-Zr-B1 | 176.2 |
| N1-Zr-B2 | 83.0 |

Example 3

Slurry-Phase Ethylene-1-Hexene Copolymerization with N-(1-methyl-1-(2-pyridyl)ethyl)-N-(2,6-diisopropylphenyl)amido Zirconium tris(tetrahydroborate)/MMAO (Al/Zr=280)

Into a 1 L stirred autoclave reactor under a nitrogen purge and maintained at temperature of 55° C. was placed 600 mL of dry hexane. 1-Hexene (43 mL), modified methylalumoxane (MMAO; 0.175 mL of 1.79 M solution in heptane, 31 equiv) and triisobutyl aluminum (2.00 mL of 0.067 M solution in hexane, 133 µmol) were added via syringe. After stirring for approximately 15 minutes, the reactor was pressurized to 85 psi with ethylene and was heated to 75° C. A catalyst solution was prepared by dissolving Into a 1 L stirred autoclave reactor under a nitrogen purge and maintained at temperature of 55° C. was placed 600 mL of dry hexane. 1-Hexene (43 mL), modified methylalumoxane (0.175 mL of 1.79 M solution in heptane, 31 equiv) and triisobutylaluminum (2.00 mL of 0.067 M solution in hexane, 133 µmol) were added via syringe. After stirring for approximately 15 minutes, the reactor was pressurized to 85 psi with ethylene and was heated to 75° C. A catalyst solution was prepared by dissolving N-(1-methyl-1-(2-pyridyl)ethyl)-N-(2,6-diisopropylphenyl)amido zirconium tris(tetrahydroborate) (4.3 mg, 10 µmol) in toluene (1 mL) and adding 1.40 mL of modified methylalumoxane (1.79 M solution in heptane, 250 equiv) with subsequent stirring for 5 minutes. The polymerization was carried out by injecting 2.4 mL of activated catalyst solution into the reactor with maintenance of the set temperature and pressure for a period of 30 minutes. The polymerization activity was calculated to be 738 g polymer mmol $Zr^{-1}$ $h^{-1}$ (100 p.s.i. ethylene)$^{-1}$.

While the present invention has been described and illustrated by reference to particular embodiments, it will be appreciated by those of ordinary skill in the art, that the invention lends itself to many different variations not illustrated herein. For these reasons, then, reference should be made solely to the appended claims for purposes of determining the true scope of the present invention.

What is claimed is:

1. A catalyst composition comprising an activator and a catalyst precursor represented by the following structure:

$$MX_xY_yZ_z$$

wherein M is a Group 4, 5 or 6 metal, X, Y and Z are groups independently bound to M; and x, y and z are each 0 or an integer from 1 to 3, provided that the net charge of the catalyst precursor is zero; wherein:

(a) X is a moiety having the formula $AR_4$; wherein A is a Group 13 element and each R is independently selected from the group consisting of hydrogen and $C_1$ to $C_{20}$ hydrocarbyl radicals; provided that at least one R is hydrogen;

(b) Y is a bidentate group having the formula $$(T)_t\text{-}D\text{-}(E)_e\text{-}G$$

forming an independent bidentate ligand bound to M through the D group and the G group, wherein:

(i) D is selected from the group consisting of boron, carbon, silicon, nitrogen, phosphorous, oxygen and sulfur;

(ii) G represents a mono- or polycyclic radical comprising an atom Q, where Q is selected from the group consisting of nitrogen, oxygen, phosphorous and sulfur;

(iii) E is a divalent $C_1$ to $C_{10}$ hydrocarbon group, where e is 0 or 1; and (iv) T is a hydrocarbon or heteroatom-containing hydrocarbon bound to D, where t is a number sufficient to satisfy the valency of the group D; and (c) Z is selected from the group consisting of halogens, alkyls, aryls, amides, phosphides, sulfides, silylalkyls and carboxylates.

2. The catalyst composition of claim 1, wherein z is 0.

3. The catalyst composition of claim 1, wherein A of (a) is boron.

4. The catalyst composition of claim 3, wherein at least two R groups of (a) are hydrogen.

5. The catalyst composition of claim 1, wherein the group G comprising Q of (b)(ii) is selected from the group consisting of pyridyl, pyrazyl and quinolyl groups.

6. The catalyst composition of claim 1, wherein the E group of (b)(iii) is selected from the group consisting of radicals: $(CR^1R^2)$, $(C=CR^1R^2)$ and $(SiR^1R^2)$; wherein $R^1$ and $R^2$ are independently selected from hydrogen and $C_1$–$C_{10}$ hydrocarbyl groups.

7. The catalyst composition of claim 1, wherein the T group of (b)(iv) is selected from the group consisting of aryl groups, substituted aryl groups, heteroaryl groups and substituted heteroaryl groups; wherein the heteroaryl comprises a heteroatom selected from the group consisting of oxygen, nitrogen and sulfur; and wherein the substituents are selected from the group consisting of halogens and $C_1$ to $C_{20}$ hydrocarbyl groups.

8. The catalyst composition of claim 1, wherein the activator is an alumoxane.

9. The catalyst composition of claim 1, further comprising a support.

10. The catalyst composition of claim 1, wherein D is nitrogen.

11. The catalyst composition of claim 1, wherein the catalyst precursor is:

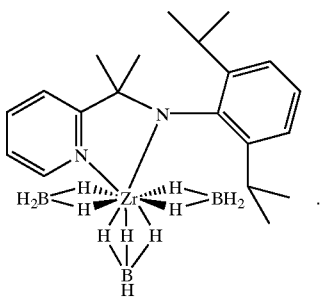

* * * * *